(12) United States Patent
Damgaard et al.

(10) Patent No.: US 7,215,988 B1
(45) Date of Patent: May 8, 2007

(54) SENSOR FOR MEASURING TISSUE PERFUSION

(76) Inventors: Lars Riis Damgaard, Vesterbrogade 6B, st.tv., DK-8000 Arhus C (DK); Jens Kristian Gundersen, Soskraenten 29, DK-8260 Viby (DK); Lars Hauer Larsen, Overdrevet 25, DK-8382 Hinnerup (DK); Thomas Kjaer, Sjaelor Boulevard 89, st.tv., DK-2500 Valby (DK)

(*) Notice: Subject to any disclaimer, the term of this patent is extended or adjusted under 35 U.S.C. 154(b) by 0 days.

(21) Appl. No.: 10/088,582

(22) PCT Filed: Oct. 4, 1999

(86) PCT No.: PCT/DK99/00522

§ 371 (c)(1),
(2), (4) Date: Jul. 1, 2002

(87) PCT Pub. No.: WO01/24692

PCT Pub. Date: Apr. 12, 2001

(51) Int. Cl.
*A61B 5/00* (2006.01)
*A61B 5/05* (2006.01)

(52) U.S. Cl. ...................... 600/358; 600/363
(58) Field of Classification Search ........ 600/345–350, 600/504–507, 363
See application file for complete search history.

(56) References Cited

U.S. PATENT DOCUMENTS

| | | | |
|---|---|---|---|
| RE30,317 E | * | 7/1980 | Lubbers et al. ............ 600/363 |
| 5,594,179 A | | 1/1997 | Marsh |
| 6,234,004 B1 | * | 5/2001 | Revsbech et al. ............ 73/19.1 |

FOREIGN PATENT DOCUMENTS

| | | |
|---|---|---|
| EP | 0549394 | 6/1993 |
| EP | 0549394 A1 | 6/1993 |
| EP | 0747675 A2 | 12/1996 |
| WO | 9516392 | 6/1995 |
| WO | PCT/US94/13243 | 6/1995 |
| WO | 9719345 | 5/1997 |
| WO | PCT/DK96/00488 | 5/1997 |
| WO | 9746853 | 12/1997 |
| WO | PCT/DK97/00250 | 12/1997 |
| WO | 98 59240 | 12/1998 |
| WO | PCT/GB98/01783 | 12/1998 |

OTHER PUBLICATIONS

Acta Physiol. scand. vol. 66:3, Blood Flow Through Human Adipose Tissue Determined with Radioactive Xenon.

* cited by examiner

*Primary Examiner*—Robert L. Nasser
(74) *Attorney, Agent, or Firm*—Robert F. I. Conte; Barnes & Thornburg LLP

(57) ABSTRACT

The invention relates to a method and a sensor for measurement of tissue perfusion. The sensor is provided with a reservoir (4) for a fluid or gaseous tracer and a tracer-permeable barrier (3), a sub-surface of which is in contact with the surrounding tissue and another sub-surface of which is in contact with a detection cavity (5) which is connected to a suitable apparatus for the measurement of tracer concentration in the detection cavity. The concentration of the tracer in the detection cavity is a measure of perfusion in the surrounding tissue. According to another embodiment of the invention it is also possible to carry out measurements of perfusion in the surface layers of the skin or of an organ.

20 Claims, 6 Drawing Sheets

SENSOR FOR MEASURING TISSUE PERFUSION

TECHNICAL FIELD OF THE INVENTION

The present invention relates generally to devices for measurements of tissue perfusion according to the preamble of independent claim 1 and more particularly to a sensor for measurement of tissue perfusion over a given variable region and having a short response time.

BACKGROUND ART

Tissue perfusion is a measure of the amount (volume) of blood passing through a unit quantity of the tissue and is often measured with the unit ml blood/100 g tissue. Since all blood tissues are at the same time being supplied with nutrients and excrete waste products through diffusion between tissue cells and the blood, tissue perfusion is a very important factor indicating the state of health of a tissue. A method for the measurement of tissue perfusion is therefore highly pertinent, for instance for monitoring tissue during and after surgical operations and transplantations. Monitoring of potentially threatened tissue, e.g. muscular tissue, whose blood supply may become adversely affected by increasing pressure in the connective tissue membrane of the muscle, would be highly pertinent as an indication of when a pressure relieving operation should be initiated. Likewise monitoring of internal perfusion caused by the formation of oedemas in a heart stopped during operation could provide valuable information about the need of external supply of nutrients to the tissue of the heart. Within medical research, perfusion is an important parameter too.

A number of methods for determination of tissue perfusion are known. A technique consisting of an injection into the relevant tissue of radioactive xenon as a tracer and measuring the decay of radioactivity as a function of time has been described (see Larsen et al., 1966. Blood Flow through Human Adipose Tissue Determined with Radioactive Xenon. Acta physiol. scand. 66, pp 337–345), but this technique suffers from a number of drawbacks in that its temporal resolution only amounts to approximately half an hour which is insufficient in many situations. Furthermore the location of the injection of the radioactive matter into the tissue relative to the location where the radioactivity is being measured is not particularly well-defined and finally, the application of radioactive matter per se involves potential hazards.

Another method of measuring tissue perfusion utilises continuous injection of ethanol during microdialysis. During microdialysis a fluid is being pumped very slowly through a fibre inserted into the tissue of the patient. The concentration of the fluid is in equilibrium with the surrounding tissue as the catheter is diffusion-open and the fluid is being collected via a return fibre. This method also suffers from an insufficient temporal resolution.

WO 97/46853 discloses a method and a microsensor which is able to measure tissue perfusion. The sensor comprises a tracer-permeable insert placed in a mouth of a tracer reservoir confined by a container, whereby said insert forms a permeable wall portion of the reservoir. A sensoric tip of a transducer is placed inside the insert or immediately outside of the latter. From the specification as a whole it appears that the tip of the transducer is very small, a diameter of 2 μm being mentioned. Consequently the transducer detects or measures the tracer concentration or pressure in a single point or in an extremely limited area. This also applies, if the transducer is provided with an inner cylindrical cavity, which is closed by the permeable insert or by a separate membrane forming the end wall of the transducer.

In connection with monitoring tissue perfusion for instance during surgical operations, the above-mentioned prior art suffers from the drawbacks of either insufficient temporal resolution or a very limited measurement space.

DISCLOSURE OF THE INVENTION

In order to circumvent the drawbacks and limitations of methods and devices for the measurement of tissue perfusion of prior art as mentioned above, it is the object of the present invention to provide a device (sensor) for the measurement of tissue perfusion which is able to integrate measurements of tissue perfusion over a larger region in the tissue, the dimensions of which region can be varied as desired.

It is a further object of the present invention to provide a device with a response time not exceeding a few minutes.

It is a further object of the present invention to provide at least one embodiment of the general inventive idea which makes it possible to carry out non-invasive measurements of skin perfusion or measurements of prefusion in the surface layers of an organ, for instance for assessment of insufficient blood circulation.

These objects are accomplished with a device (sensor) according to the characterising clause of claim 1.

Various advantageous embodiments of the invention are defined in the dependent claims.

In the sensor for tissue perfusion according to the invention a fluid or gaseous tracer from a suitable supply means is supplied to a reservoir in which a constant high concentration of the tracer is maintained through diffusion from the supply means and from which reservoir a small portion of the tracer molecules will diffuse into a tracer-permeable barrier which is partly in contact with the surrounding tissue. From this barrier, part of the tracer molecules will move out into the surrounding tissue via a first spatially extended area, whereas another portion of the tracer molecules will move into an adjoining detector cavity via a second spatially extended area, said detector cavity being in communication with a suitable detector apparatus measuring the concentration of tracer in the detection cavity. The movement of tracer molecules from the reservoir into the surrounding tissue thus takes place via a tracer-permeable barrier which is in contact with the surrounding tissue via said first spatially extended area and the portion of the tracer molecules moving into the detection cavity arrives at the detection cavity via a tracer-permeable barrier and said second spatially extended area. Said first area thus constitutes the area of contact between said tracer-permeable barrier and the surrounding tissue, whose perfusion is to be measured, whereas said second area constitutes the area through which tracer molecules are able to reach the detection cavity. The distribution between the diffusion to the surrounding tissue and the diffusion to the detection cavity will be determined by the flow of dissolve matter in the surrounding tissue, i.e. the perfusion, such that if the transport in the tissue is of large magnitude only a small portion of the tracer will diffuse into the detection cavity and vice versa. The signal from the detection apparatus will thus become a measure of tissue perfusion in the region surrounding the fibre.

According to the present invention the dimensions of the contact region between said tracer-permeable barrier and the surrounding tissue can be varied and thereby the region over which the tissue perfusion measurement is being carried out. It is also possible to vary the second area providing access to the detection cavity. By varying the geometry of the sensor, i.e. the relative layout of the reservoir, barrier and detection cavity, it is possible to vary the sensitivity and the radial resolution of the measurements being performed. It is furthermore possible to utilise a mixture of at least two tracers which might be supplied and removed substantially momentarily. A time-based measurement after instantaneous supply/removal to/from the tracer reservoir of two tracers with different diffusion coefficients will make it possible to distinguish between how much of the diffusion of the tracers away from the tracer reservoir is due to the concentration gradient within the tissue and how much is due to the transportation of the tracers away from the tissue by the blood. Thus, independent measures of perfusion and of diffusion coefficients within the tissue can be obtained.

It is furthermore possible to carry out measurements of $O_2$ and $CO_2$ and other gasses present in the tissue simultaneously with tissue perfusion.

As a suitable tracer for tissue perfusion measurements for instance helium, argon or hydrogen could be used, but it would also be possible to use other tracers.

Finally for in-situ calibration purposes the patient can inhale a gas which is being detected by the sensor placed in the tissue.

BRIEF DESCRIPTION OF THE DRAWINGS

The invention will now be described by way of exemplifying embodiments hereof and with reference to the accompanying drawings in which FIG. 1a is a longitudinal section of a first embodiment of a sensor according to the present invention;

FIG. 1b is a cross section along the line indicated by A—A in FIG. 1a;

FIG. 2a is a longitudinal section of a second embodiment of a sensor according to the present invention;

FIG. 2b is a cross section along the line indicated by B—B in FIG. 2a;

DESCRIPTION OF THE PREFERRED EMBODIMENTS

In the following detailed part of the present description a number of different embodiments of the present invention will be described with reference to the accompanying drawings, but it is understood that these embodiments only constitute examples of the general inventive idea, and that other embodiments may be conceivable by a person skilled in the art.

Figure 1:
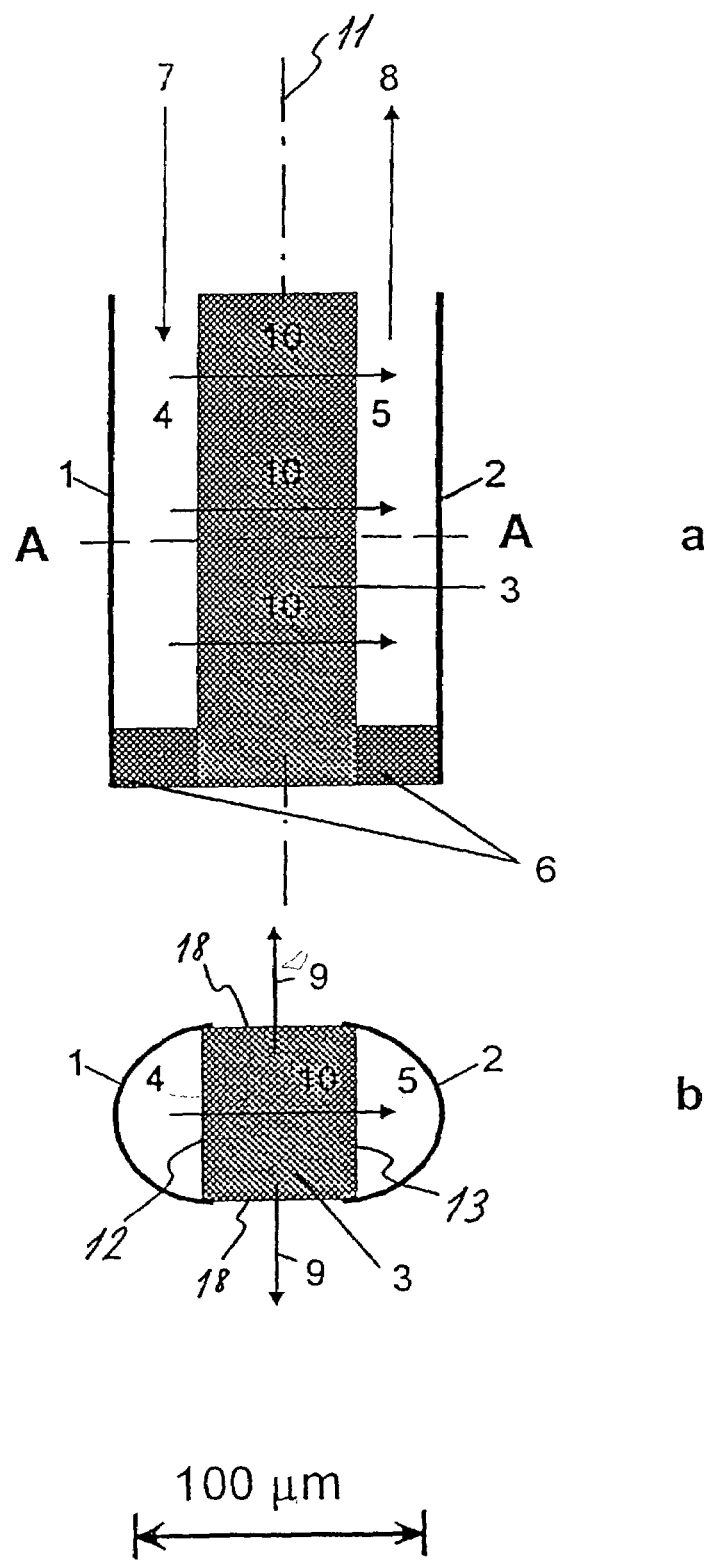

The first embodiment of the sensor is shown in FIG. 1a and FIG. 1b. The sensor is substantially symmetrical about a vertical plane 11 and comprises two U-shaped profiles 1, 2, the reservoir profile 1 and the detection profile 2 made of a gas-impermeable material such as metal or a suitable plastic material. The open sides 12, 13 of these two profiles 1, 2 are both in sealing abutment with a barrier 3 disposed between the reservoir 4 and the detection cavity 5 and extending throughout the vertical length of the sensor. The barrier 3 is made from a gas-permeable material, such as silicon or Teflon, such that two cavities, the reservoir 4 and the detection cavity 5, are defined. At the distal end hereof both the reservoir 4 and the detection cavity 5 are closed by a gas-impermeable barrier 6. At its proximal end the reservoir 4 is provided with an open inlet 7 which via a tube (not shown) is in communication with a supply container (also not shown) containing a gaseous tracer (for instance helium). The outer walls of both the tube and the container are made from a gas-impermeable material. The detection cavity 5 is at its proximal end provided with an open outlet 8 which via a tube (not shown) is in communication with a detector apparatus (vacuum pump and mass spectrometer as it is well-known within the art). The tube between the outlet 8 and the detector apparatus is made from a gas-impermeable and pressure resistant material. The reservoir profile 4, the detection cavity profile 5 and the barriers 3, 6 will in the following be referred to as the fibre.

The fibre is designed to be positioned within the tissue of a patient whose perfusion in that part of the tissue is to be measured. The functional principle of the invention is that a constantly high concentration of the tracer is maintained in the reservoir 4, the concentration being maintained via diffusion from the supply container. A small portion of the molecules of the tracer will due to diffusion move from the reservoir 4 out into the gas-permeable barrier 3 and a portion hereof will move out into the surrounding tissue through a first area 18, as indicated by the arrows 9, while another portion will move into the detection cavity 5 through a second area 13, as indicated by the arrows 10, and eventually be detected by means of the detection apparatus. The distribution between the diffusion to the surrounding tissue and the diffusion to the detection cavity 5 will be determined by the transport of dissolved matter in the surrounding tissue, such that if the transport in the tissue is of a large magnitude only a small portion of the tracer will diffuse into the detection cavity 5 and vice versa. The signal from the detection apparatus will thus become a measure of tissue perfusion in the region surrounding the fibre.

Figure 2:
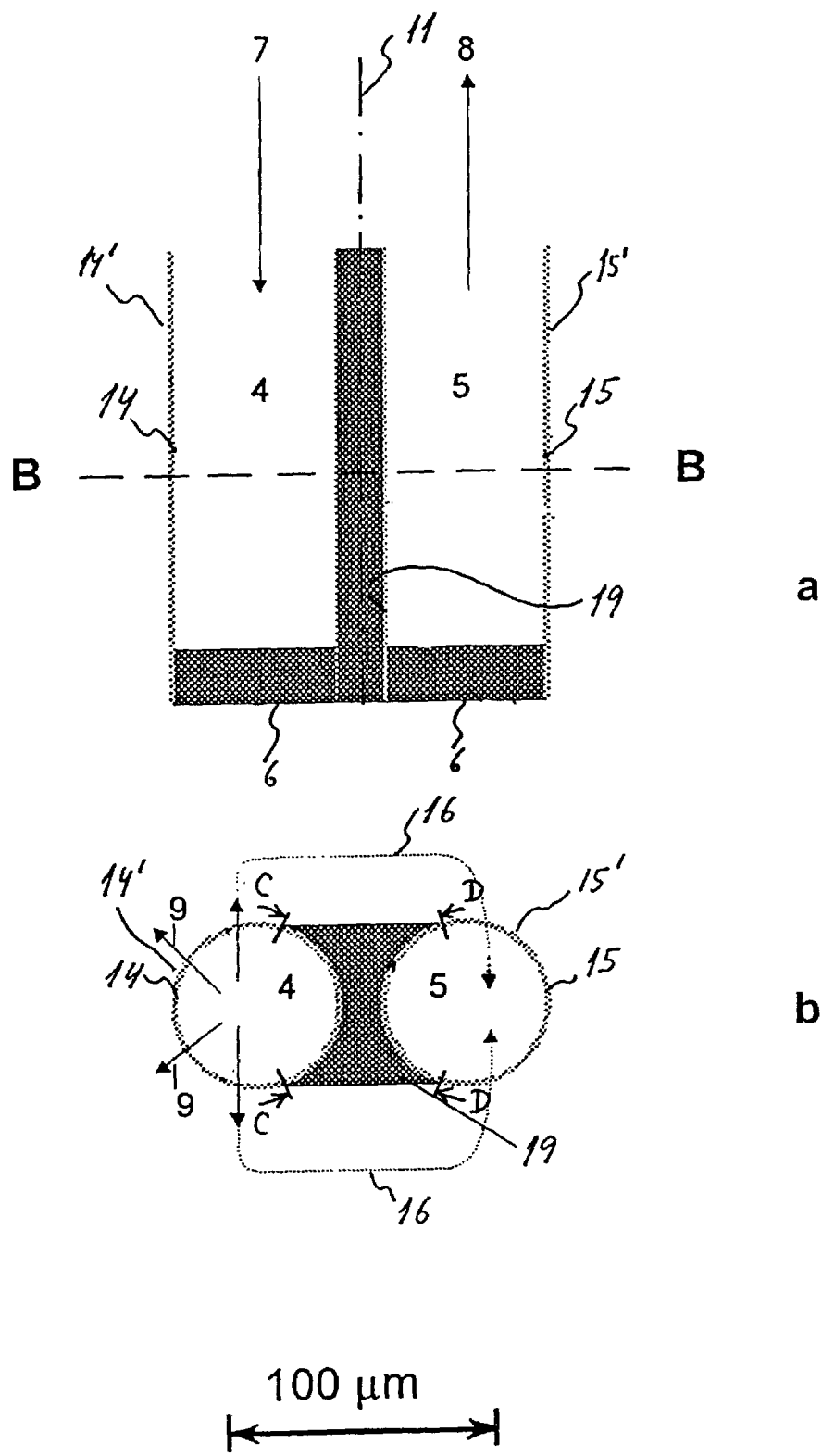

FIG. 2a and FIG. 2b show a second embodiment of the present invention. Throughout the following description of the second embodiment of the present invention, elements identical with elements of the first embodiment shown in FIG. 1a and FIG. 1b will be designated by the same reference numerals as on FIG. 1a and FIG. 1b. The second embodiment is also substantially symmetrical about a vertical plane 11 and comprises two tubes: the reservoir tube 14 defining the reservoir 4 and the detection tube 15 defining the detection cavity 5, both tubes being made from a semi-gas-impermeable material (plastics). These two tubes 14, 15 are separated from each other by a barrier 19 made from a gas-impermeable material, such as metal or plastics. At the distal end, both the reservoir 4 and the detection cavity 5 are closed by a gas-impermeable barrier 6. At its proximal end the reservoir tube 14 is provided with an open inlet 7 which via a tube with gas-impermeable wall (not shown) is in communication with a supply container constructed from a gas-impermeable material containing a gaseous tracer (for instance helium). The detection tube 5 is at its proximal end provided with an outlet 8 communicating via a pressure resistant tube with gas-impermeable wall with a detection apparatus (vacuum pump and mass spectrometer as it is well-known within the art). The reservoir tube 14, the detection tube 15 and the barriers 6, 19 will in the following be referred to as the fibre.

The fibre is designed to be positioned within the tissue of a patient whose perfusion in that part of the tissue is to be measured. The functional principle of the invention is that a constantly high concentration of the tracer is maintained in the reservoir 4, the concentration being maintained via diffusion from the supply container. A small portion of the molecules of the tracer will due to diffusion move from the reservoir 4 out through the wall of the reservoir tube 14 through a first area 14' (as delimited by the two arrows C in FIG. 2b) and into the surrounding tissue, as indicated by the arrows 9. Of this quantity of tracer, a portion will diffuse into the detection tube and pass through the wall (15) through a second area 15' (as delimited by the two arrows D in FIG. 2b) to the detection cavity 5 as indicated by the arrows 16, from where it will be detected by the detection apparatus. The quantity reaching the detection cavity will depend on the transport conditions in the tissue through which diffusion takes place, and the signal from the detector will thus be a measure of the transport conditions, i.e. the perfusion, in the region around the fibre.

A third embodiment (not shown) of the present invention is directly derivable from the two first embodiments described above in that the structures shown in FIG. 1 and FIG. 2 are helically wound around the longitudinal axis 11 of the fibres. This has the effect of making the sensitivity of the fibres in a plane perpendicular to the longitudinal axis omnidirectional. A suitable pitch of the helix could for instance constitute 10 revolutions per cm.

Figure 3:
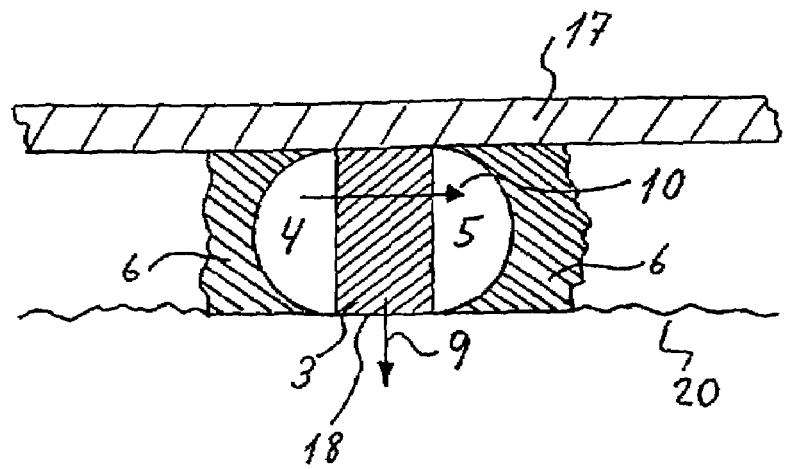
FIG. 3a is a side elevation cross-sectional view of a first version of a fourth embodiment of the present invention.
FIG. 3b is a side elevation cross-sectional view of a second version of a fourth embodiment of the present invention.
Figure 3:
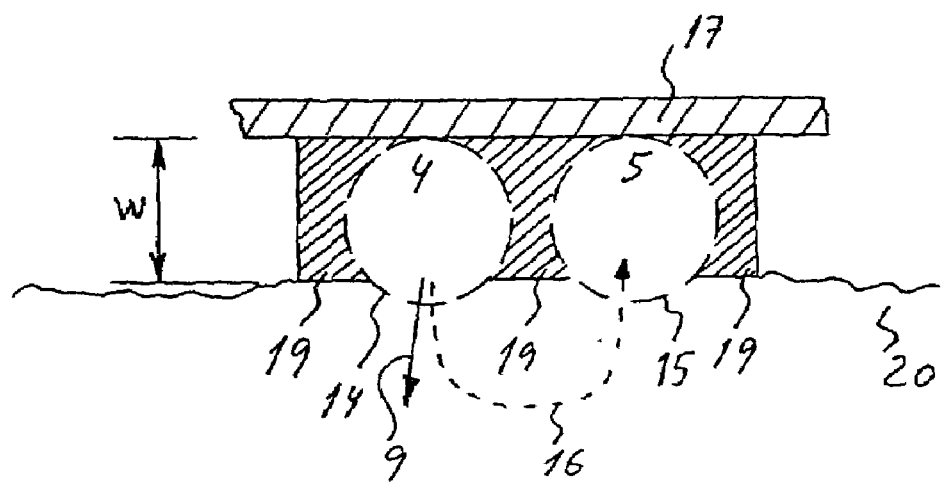

FIGS. 3a and 3b show a fourth embodiment of the present invention which differs significantly from the three previous embodiments described above. Where the three above embodiments were designed to be inserted into the tissue, the fourth embodiment of the present invention is fastened non-invasively on the surface (20) of the skin or of an organ of a patient to provide the possibility of carrying out measurements of perfusion in the surface layers of the skin or the organ such as carried out for the assessment of insufficient blood circulation in for instance a leg of the patient.

The operational principle of the first version of the fourth embodiment shown in FIG. 3a corresponds to the operational principle of the first embodiment shown in FIG. 1a and FIG. 1b. The operational principle of the second version of the fourth embodiment shown in FIG. 3b corresponds to the operational principle of the second embodiment shown in FIG. 2a and FIG. 2b.

In the embodiment shown in FIG. 3a, the inner side, i.e. the side facing the surface (20) of the skin or organ of the patient, of a gas-impermeable disc 17 is provided with a single one of the sensors according to the first embodiment of the present invention shown in FIG. 1a and FIG. 1b. The longitudinal axis 11 of the sensor extends substantially parallel with the plane of said disc 17 and one of the sides 18 of the tracer-permeable barrier 3 is in contact with the surface (20) of the patient's skin or organ. Diffusion of tracer molecules from the barrier 3 into the skin or organ thus only takes place via this single side 18. The function of the disc 17 is to enable sufficient contact pressure between fibre and skin or organ and to prevent escape of tracer molecules in the direction opposite the skin or organ.

In the embodiment shown in FIG. 3b the inner side, i.e. the side facing the surface (20) of the skin or organ of the patient, of a gas-impermeable disc 17 is provided with a single one of the sensors according to the second embodiment of the present invention shown in FIG. 2a and FIG. 2b. The longitudinal axis 11 of the sensor extends substantially parallel with the plane of said disc 17 and parts of the tracer-permeable walls 14 and 15 of the reservoir 4 and detection cavity 5, respectively, are in contact with the surface of the patient's skin or organ. The width w of the tracer-impermeable barrier is modified compared to the second embodiment in order to provide a contact area of sufficient size between the reservoir 4 and the surface of the skin or organ and between the detection cavity 5 and the skin or organ, respectively. Also the side of the reservoir 4 facing away from the detection cavity 5 and the side of the detection cavity 5 facing away from the reservoir 4 are covered with tracer-impermeable barriers 19.

Figure 4:
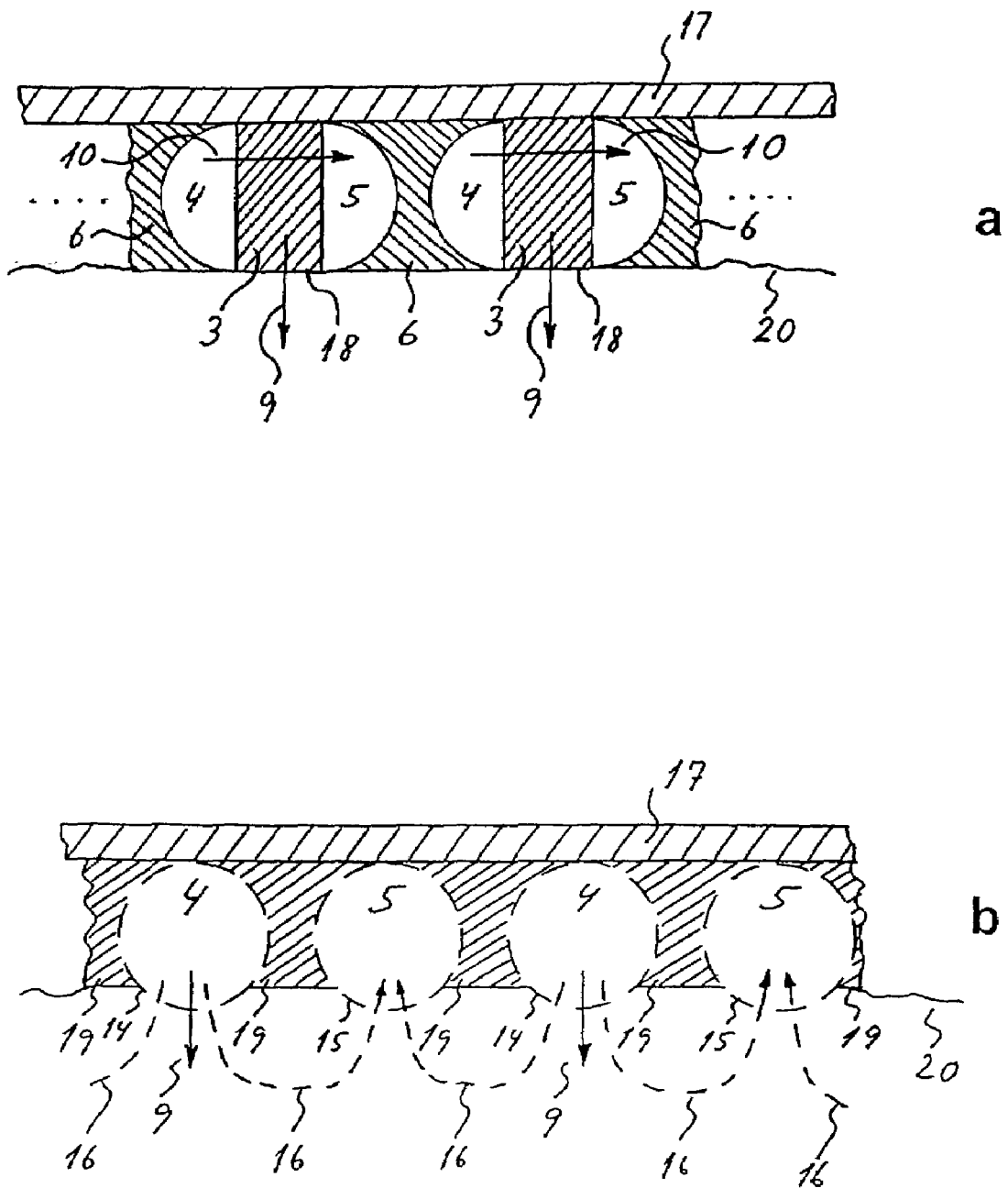
FIG. 4a is a side elevation cross-sectional view of a first version of a fifth embodiment of the present invention comprising interlaced reservoir- and detection cavity sections.
FIG. 4b is a side elevation cross-sectional view of a second version of a fifth embodiment of the present invention comprising interlaced reservoir- and detection cavity sections.

A more preferable variation of the embodiments shown in FIG. 3a and FIG. 3b is shown in FIG. 4a and FIG. 4b. The difference between the embodiments shown in FIGS. 3a/3b and FIGS. 4a/4b is that both the reservoir 4 and the detection cavity 5 in the embodiments shown in FIG. 4a and FIG. 4b are split up into a plurality of substantially identical reservoir/detection cavity sub-systems covering a substantial part of the inner side of said gas-impermeable disc 17. The functional principles of the embodiments shown in FIG. 4a and FIG. 4b correspond to those described in connection with the preceding embodiments and will hence not be described in detail here.

In the embodiments of the present invention according to FIGS. 3a, 3b, 4a and 4b it is possible to provide the inner side of the disc 17 with a system of partially open channels where the openings are in contact with the surface 20 of the patient's skin or organ, and where the channels can be connected to a suitable vacuum source. Application of vacuum to the channels ensures a firm attachment of the disc 17 to the skin or organ of the patient.

Figure 5:
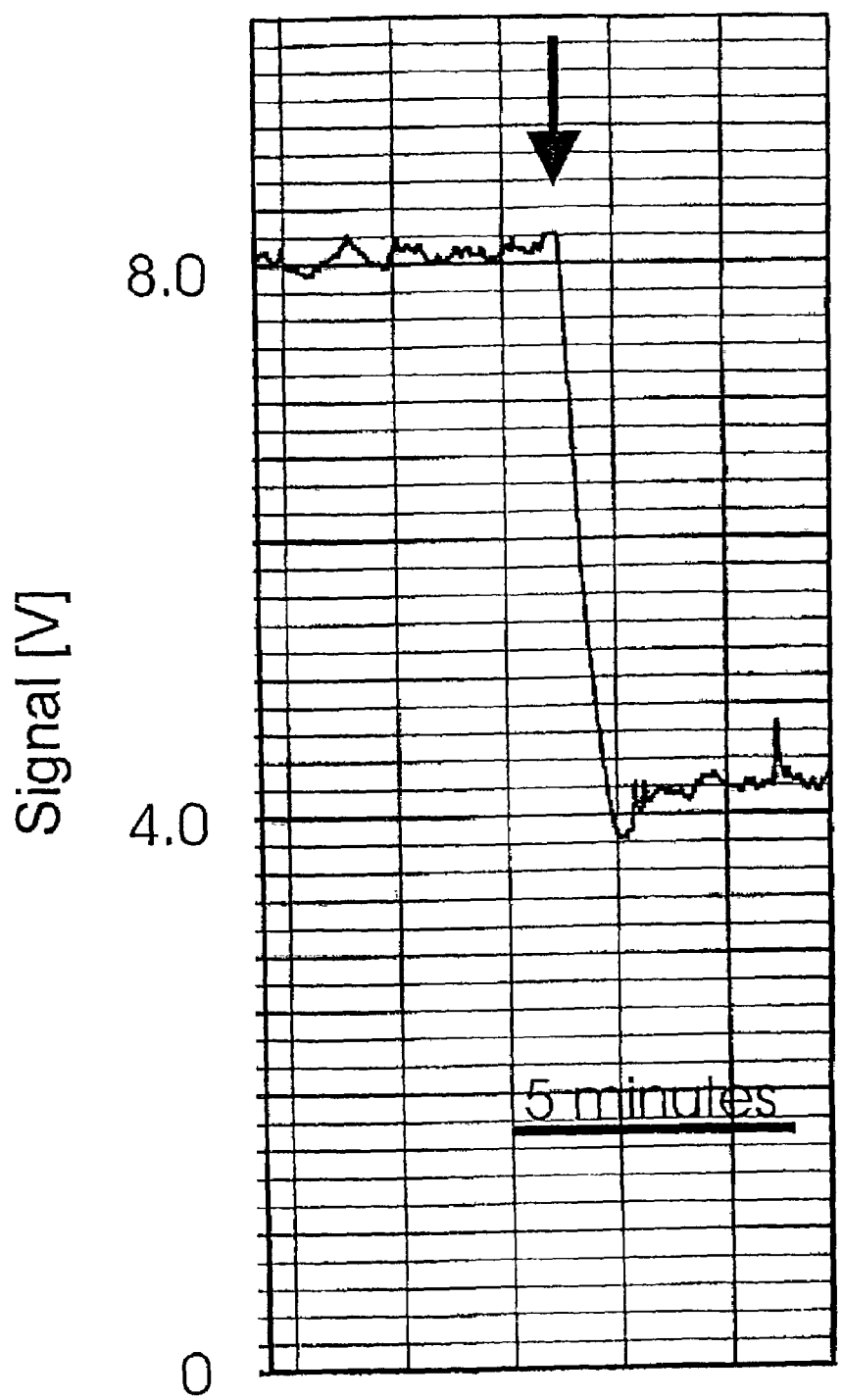
FIG. 5 is the response of a microsensor according to the invention as a function of time for a sudden change of perfusion obtained in a specific experiment.

FIG. 5 shows the response of the sensor in volts as a function of time obtained in an experiment where water moves through a sand-filled tube simulating a bloodflow through tissue. The velocity of the water changed suddenly from 4.8 micrometers/second to the left of the arrow in the Figure to 24.8 micrometers/second immediately to the right of the arrow. A response time of approximately 0.5–1.0 minutes is possible, although the response time varies as a function of perfusion, and increases when the velocity through the tissue changes from a relatively high level to a relatively low level and vice versa.

Figure 6:
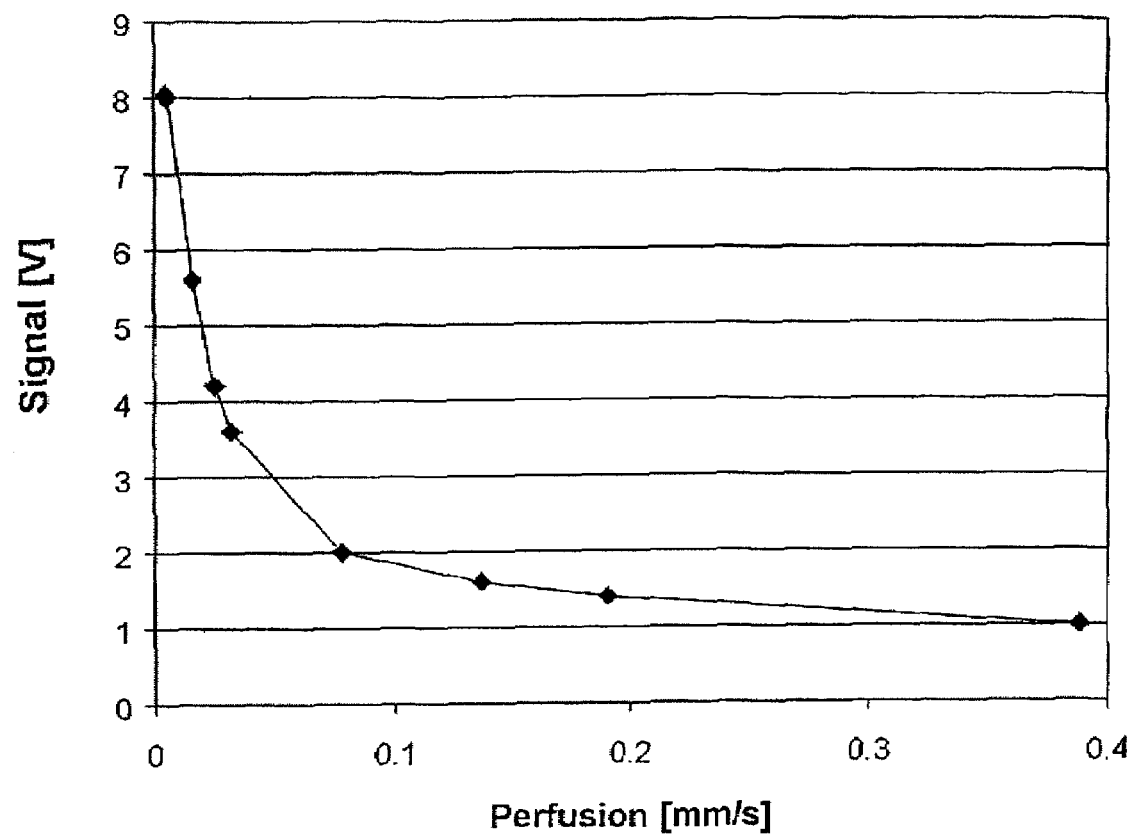
FIG. 6 is a calibration curve of the sensor, i.e. the signal from the sensor as a function of the velocity of water obtained in the same experiment as mentioned in connection with FIG. 5.

FIG. 6 shows a calibration curve obtained in the same experiment as in FIG. 5, i.e. a curve of the signal from the detection device in Volts as a function of the velocity of water in mm/second.

Above, a number of different embodiments of the present invention have been shown and described, but it is understood that these embodiments only constitute examples of the general inventive idea as defined in the accompanying claims, and that other embodiments of the present invention might be conceivable by a person skilled in the art.

The invention claimed is:

1. Sensor for the measurement of tissue perfusion where a fluid or gaseous tracer is being supplied from a tracer source via a reservoir (4) to the tissue, the perfusion and of which is to be measured, and detected by a detection device via a detection cavity (5) comprising:

said reservoir (4) having a reservoir wall with a tracer-permeable reservoir wall portion that permits tracer to be supplied from the reservoir to surrounding tissue, said detection cavity having a detection cavity wall having a tracer-permeable detection cavity wall portion, said tracer-permeable reservoir wall portion and the tracer-permeable detection wall portion respectively, communicating with the surroundings, such that a part of the tracer leaving said reservoir (4) can arrive at said detection cavity (5), the reservoir and the detection cavity are mutually interspaced, elongated cavities and the tracer-permeable reservoir wall portion and the tracer permeable detection cavity wall portion are elongated side wall portions.

2. Sensor according to claim 1, wherein said reservoir (4) communicates partly with said surrounding tissue through a spatially extended tracer-permeable barrier (3), having a first surface (18) which forms a first area, and partly with said detection cavity (5) through the same spatially extended tracer permeable barrier (3), having a second surface (13) which forms a second area, said tracer-permeable barrier is a common permeable wall for said reservoir and said detection cavity, said detection cavity wall is distinct from said common permeable wall, and said reservoir wall is distinct from said common permeable wall.

3. Sensor according to claim 1, wherein said reservoir (4) communicates with said surrounding tissue through a spatially extended tracer-permeable barrier (14), a first surface (14') of which forms a first area, and partly with said detection cavity (5) via said tissue and through another spatially extended tracer-permeable barrier (15), a second surface (15') of which forms a second area.

4. Sensor according to claim 1, wherein said reservoir (4) and said detection cavity (5) are separated by a barrier (3, 19), and the reservoir (4), barrier (3, 19) and cavity (5) are built together to form a longitudinal sensor.

5. Sensor according to claim 1, wherein said reservoir (4), said detection cavity (5) are separated by spatially extended tracer-permeable barriers (3, 14, 15) are adapted to be located between a large surface of a tracer-impermeable panel or disc (17) and the surface (20) of the skin or organ of a patient, the perfusion of the surface layers of which skin or organ is to be measured, and a longitudinal axis 11 extending substantially parallel with said large surface of the panel or disc (17), such that said spatially extended tracer-permeable barriers (3, 14, 15) are partly in contact with the surface of the skin or organ, and such that tracer can move from said reservoir (4) into said skin or organ and either from here into said detection cavity (5), or directly from said reservoir (4) into said detection cavity (5).

6. Sensor according to claim 4, wherein a series of said reservoir (4), said detection cavity (5) and said tracer-permeable barriers (3, 14, 15) are placed in side-by-side relationship with each other to cover a larger area of tissue.

7. Sensor according to claim 6, wherein said series of reservoirs (4), detection cavities (5) and tracer-permeable barriers (3, 14, 15) are located along one of the large sides of said panel or disc (17), such that they cover a substantial part of said side, and such that parts of said tracer-permeable barriers (3, 14, 15) can be brought into contact with the surface of the skin or organ of the patient.

8. Sensor according to claims 5 or 7, wherein said panel or disc (17) on the side facing the surface (20) of the skin or organ is provided with a pattern of partially open channels which can be connected to a vacuum source.

9. Sensor according to claim 6, wherein said series of reservoirs, detection cavities and tracer-permeable barriers are located along one of the large sides of said panel or disc, such that they cover a substantial part of said side, and such that parts of said tracer-permeable barriers can be brought into contact with the surface of the skin or organ of the patient.

10. Sensor according to claim 1, characterized in, that the reservoir (4) and the detection cavity (5) are cylindrical and arranged in parallel.

11. Sensor according to claim 1 or 10, characterized in that the tracer-permeable wall portion (14') of the reservoir (4) and the tracer permeable wall portion (15') of the detection cavity (5) are separate, mutually interspaced wall portions.

12. Sensor according to claim 11, characterized in that the reservoir (4) and the detection cavity (5) are separated by a tracer-impermeable barrier (19).

13. Sensor according to claim 11, characterized in that the reservoir (4) is defined by a tracer-permeable, tubular body (14) and that the detection cavity (5) is defined by a tracer-permeable, tubular body (15), and further that two bodies (14, 15) are interconnected by means of the tracer-impermeable barrier (19).

14. Sensor according to claim 1 or 10, characterized in that the tracer-permeable wall portion of the reservoir (4) and the tracer-permeable wall portion of the
detection cavity (5) both are formed by a common tracer-permeable barrier (3) made from a tracer-permeable material, said tracer-permeable barrier (3) having a first longitudinally extending surface (18) being in contact with the surroundings, a second longitudinally extending surface (13) defining a portion of the detection cavity (5) and a third longitudinally extending surface (12) defining a portion of the tracer reservoir (4).

15. Sensor according to claim 14, characterized in that the tracer reservoir (4) is partly defined by a substantially U-shaped profile member (1), and that the detection cavity (5) is partly defined by a substantially U-shaped profile member (2) and further that the tracer-permeable barrier (3) sealingly engages the U-shaped profile members (1, 2) so as to close open sides (12, 13) thereof.

16. Sensor according to claim 1, characterized in that the tracer-permeable reservoir wall portion (3; 14') and the tracer-permeable detection cavity wall portion (3; 15') extend substantially over the entire length of the sensor.

17. Sensor according to claim 1, characterized in that the sensor is substantially symmetrical about a longitudinal plane (11).

18. Sensor according to claim 1, characterized in that it comprises a series of reservoirs (4) and detection cavities (5) placed in side-by-side relationship.

19. Sensor for the measurement of tissue perfusion where a fluid or gaseous tracer is being supplied from a tracer source via a reservoir (4) to the tissue, the perfusion of which is to be measured, and detected by a detection device via a detection cavity (5), comprising:
a reservoir;
a detection cavity;
a first tracer permeable barrier arranged such that the supply of tracer from said reservoir to the surrounding tissue takes place via a spatially extended first area;
a second tracer permeable barrier arranged such that a part of the tracer molecules leaving said reservoir arrive at said detection cavity via a spatially extended second area;

said reservoir and said detection cavity are separated by a third barrier;

the reservoir, the first and second tracer-permeable barriers, the third barrier, and the detection cavity are built together to form a longitudinal sensor; and a tracer impermeable panel or disc on one side of the longitudinal sensor, where the panel or disc has at least opposing large surfaces, wherein said reservoir, said detection cavity and said first second-permeable barriers, and third barrier are adapted to be located between a surface of a tracer-impermeable panel or disc and a surface of said tissue, with a surface of the panel or disc facing the tissue, such that a longitudinal axis of the sensor is substantially parallel with said large surface of the panel or disc, and further such that said spatially extended tracer-permeable barriers would be partly in contact with the surface of the skin or organ, and such that tracer can move from said reservoir into said skin or organ and from there into said detection cavity, or directly from said reservoir into said detection cavity;

and said panel or disc on the side that faces surface of the tissue when in use is provided with a pattern of partially open channels which can be connected to a vacuum source.

20. Sensor according to claim 19 wherein a series of said reservoir, said detection cavity and said tracer-permeable barriers are placed in side-by-side relationship with each other to cover a larger area of tissue.

* * * * *